United States Patent [19]

Sterling et al.

[11] Patent Number: 4,758,382
[45] Date of Patent: Jul. 19, 1988

[54] PROCESS FOR THE STEREOSPECIFIC PREPARATION OF 24(R),25- AND 24(S),25-DIHYDROXYCHOLECALCIFEROL AND NOVEL INTERMEDIATES USED THEREFOR

[75] Inventors: Jeffrey Sterling; Ben-Zion Weiner; Dinora Barasch; Danielle Hirsch, all of Jerusalem; Eliot Slovin, Ra'anana, all of Israel

[73] Assignee: Teva Pharmaceutical Industries Ltd., Israel

[21] Appl. No.: 944,921

[22] Filed: Dec. 22, 1986

[30] Foreign Application Priority Data

Jan. 21, 1986 [IL] Israel ........................................ 77668

[51] Int. Cl.$^4$ ................................................ C07J 9/00
[52] U.S. Cl. .................................................. 260/397.2
[58] Field of Search ...................................... 260/397.2

[56] References Cited

U.S. PATENT DOCUMENTS

| | | | |
|---|---|---|---|
| 3,715,374 | 2/1973 | DeLuca | 260/397.2 |
| 4,344,888 | 8/1982 | Takayama et al. | 260/397.2 |
| 4,442,093 | 4/1984 | Maeda et al. | 514/167 |

*Primary Examiner*—Leonard Schenkman
*Assistant Examiner*—Joseph A. Lipovsky
*Attorney, Agent, or Firm*—Steinberg & Raskin

[57] ABSTRACT

A novel process for the stereospecific preparation of a 24(R),25- and 24(S),25-dihydroxycholecalciferol. Also provided are novel intermediates used in the above process, being 22-p-toluenesulfonyl derivatives of 23,24,25,26,27-pentanorcholecalciferol and of 24(R)- and 24(S),25-dihydroxycholecalciferol.

16 Claims, No Drawings

PROCESS FOR THE STEREOSPECIFIC PREPARATION OF 24(R),25- AND 24(S),25-DIHYDROXYCHOLECALCIFEROL AND NOVEL INTERMEDIATES USED THEREFOR

FIELD OF INVENTION

The present invention relates to a novel method for the stereospecific synthesis of 24(R),25- and 24(S),25-dihydroxycholecalciferol, to novel intermediates used in that synthesis and to their preparation.

24,25-Dihydroxycholecalciferol (hereinafter "24,25(OH)$_2$D$_3$") is a metabolite of vitamin D$_3$ known to possess physiological activity related to that of vitamin D$_3$. Thus Edelstein, et al. (Nature 276, 517–519, (1978)) have shown that 24,25(OH)$_2$D$_3$ is essential for bone formation in chicks; and Norman et al. (Life Science, 27, 229–237, (1980)) have found it is indispensable for calcium and phosphorus homeostasis. Furthermore, Kanis et al. (Brit. Med. J., I, 1383, (1978)) suggest that 24,25(OH)$_2$D$_3$ may be an important regulator of skeletal metabolism in humans. Recently it has been claimed in U.S. Pat. No. 4,442,093 that this vitamin D$_3$ metabolite has anti-hypercalcemia, anti-ulcer and anti-tumor activities and is also active in controlling blood sugar levels in humans.

The naturally occurring metabolite 24,25(OH)$_2$D$_3$ is the 24(R) enantiomer and, as is well known, its physiological activity and, consequently, its therapeutic utility differ considerably from that of the 24(S)-isomer, which is not found in the natural metabolite, as shown by Stern et al. (Biochem. & Biophys. Res. Comm., 67, 965–971, (1975)).

DESCRIPTION OF PRIOR ART

Owing to the biological importance of 24,25(OH)$_2$D$_3$, many synthetic procedures for its preparation were proposed in the literature. However, these procedures are generally unsuitable for industrial-scale production of 24(R),25(OH)$_2$D$_3$. The majority of the aforesaid procedures are not stereospecific for the physiologically active 24(R) isomer. For example, M. Seki, et al. (Chem. Pharm. Bull. (Japan), 21, 2783, (1973)) reported a non-stereospecific synthesis of 24,25-dihydroxycholesterol starting from desmosterol, which is not commercially available. They introduced the C-24 and C-25 hydroxy groups either by epoxidation with m-chloroperbenzoic acid followed by hydrolysis or by hydroxylation with osmium tetroxide followed by reductive hydrolysis. In subsequent work Seki et al. (Tetrahedron Letters, 15, (1975)) described the resolution of these racemic epoxides by chromatographic means. Desmosterol was also the starting material used by R. Tchienehom et al. (European Patent No. 5,653) in their non-stereospecific synthesis via oxidative iodination followed by acetic acid solvolysis.

Lam et al. (Biochemistry, 12, 4851, (1973)) reported a non-stereospecific synthesis of 24,25-dihydroxycholesterol starting from 3β-acetoxy-27-nor-5-cholestene-25-one (also not commercially available), via acetylation of the enol acetate. Likewise, there are several reported syntheses involving non-stereospecific reduction of the C-24 carbonyl group of 25-hydroxy-24-oxocholesterol derivatives. Eyley, et al. (J. Chem. Soc., 727, (1976)) described the preparation of such a derivative through aldol condensation between the C-22 aldehyde and 3-methyl-3-tetrahydropyranyloxy2-butanone followed by reduction of the resulting enone. The preparation of such a ketol by C-25 oxidation of a 24-oxocholesterol derivative with subsequent non-stereospecific reduction was also reported (Japanese Pat. Nos. 80,164,700 and 55,131,000). Thus, 24,25(OH)$_2$D$_3$ in the form of a mixture of the enantiomers is comparatively easy to produce, but so far no satisfactory procedure for the separation of the isomers on an industrial scale is available.

A stereoselective synthesis of 24,25(OH)$_2$D$_3$ was reported by J. Partridge, et al. (J. Amer. Chem. Soc., 98, 3739, (1976)) consisting of stereoselective epoxidation, with tert-butyl hydroperoxide in the presence of vanadyl acetoacetate, of the cis-Δ$^\leq$-25-hydroxycholesterol derivative available from the catalytic reduction of the corresponding alkyne. This synthesis requires stereoisomeric as well as regioisomeric separation of product mixtures.

The most useful stereospecific syntheses of 24,25-dihydroxycholecalciferol known to date are based on the use of a 22-sulfonylcholesterol derivative. Takayama et al. (Tetrahedron Letters, 21, 5027, (1980)) condense such a compound with optically pure D-1,2-epoxy-3-methyl-3-butanol (prepared from D-glyceric acid). On the other hand, European Patent 063,678 teaches the condensation of a 22-sulfonylcholesterol derivative with 2,3-dihydroxypropanal-2,3-acetonide (also prepared from a D-glycerate derivative).

Even the last mentioned stereospecific syntheses have not proven to be practical for routine production, because, in common with all the other reported syntheses of 24,25(OH)$_2$D$_3$, the penultimate intermediate is a 24,25-dihydroxycholestane derivative which must be irradiated to complete the preparation of 24,25(OH)$_2$D$_3$. It is well-known that the irradiation of any such provitamin D derivative to previtamin D and the subsequent thermal isomerization of the latter to the desired vitamin D derivative are always low-yield steps affording a mixture of isomers from which the vitamin can be isolated only with great difficulty and in low yields. Efficient irradiation techniques are especially problematical for large-scale processes.

It is an object of the present invention to overcome the above drawbacks of the known procedures and to provide a novel method for the direct preparation of 24,25(OH)$_2$D$_3$ in a stereospecific manner not requiring any photochemical transformation of a provitamin to a previtamin derivative, nor any isomerization to a vitamin derivative.

Thus, in accordance with one aspect of the present invention there is provided a stereospecific process for the preparation of 24(R),25- or 24(S),25-dihydroxycholecalciferol of the general formula (I)

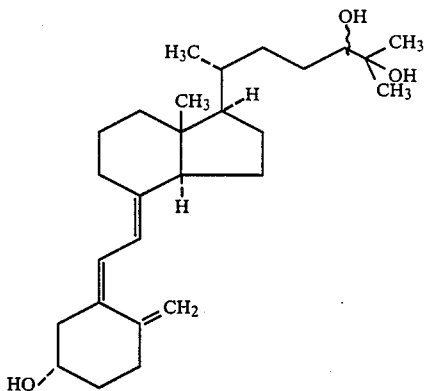

which comprises the steps of:
(a) Condensing a compound of the general formula (II)

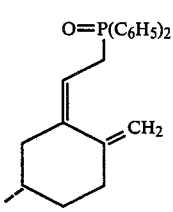

wherein
Ar is monocyclic aryl, having the (1R,6R,9R, 2′S) configuration, with the base-generated carbanion derived from a compound of the formula (III)

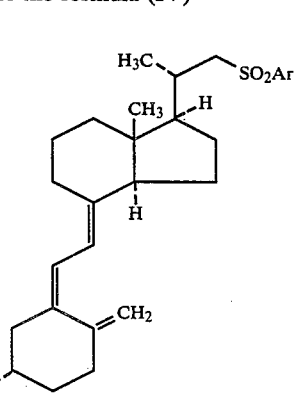

wherein
$R_1$ is a suitable base-stable hydroxy-protecting group, having the (S)-(Z) configuration, to give a compound of the formula (IV)

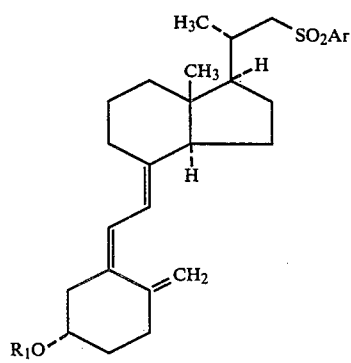

wherein
Ar and $R_1$ are as defined above;
(b) Reacting the base-generated carbanion derived from the compound of formula (IV) above with the 2(R) or 2(S) isomer of 3-methylbutane-1,2,3-triol 1-arylsulfonate of the formula (V)

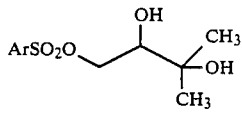

wherein,
Ar is as defined above, in the presence of a strong base, to give a compound of the formula (VI)

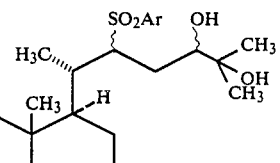

wherein
Ar and $R_1$ are as defined above;
(c) Splitting off the 22-sulfonyl group from the compound of the formula (VI) above by known methods; and
(d) Splitting off the hydroxy-protecting group $R_1$ from the compound thus obtained to yield the desired compound of formula (I) above.

The monocyclic aryl groups Ar in the compounds of the formulae (II), (IV), (V) and (VI) are suitably optionally substituted phenyl groups, preferably phenyl or p-tolyl.

As a base-stable hydroxy-protecting group $R_1$ there may be used any of such conventional groups well known in the art. As examples, there may be mentioned the methoxymethyl ether, tetrahydropyranyl ether, methylthiomethyl ether or tri-benzylsilyl ether groups, and most preferably the tert.-butyldimethylsilyl ether group.

The condensation reaction in step (a) above is preferably carried out as follows:

The compound of formula (III) is dissolved in a suitable inert aprotic solvent, preferably tetrahydrofuran, and reacted with a strong base, preferably n-butyllithium at a temperature in the range of −80° to −40° C. To the resulting solution, containing the carbanion of the compound (III), there is then added a solution of the compound of formula (II) in the same solvent, and the reaction is allowed to proceed as in a Wittig reaction, at an appropriate temperature in the range of −60° to 20° C.

It was quite surprising to find, in accordance with the present invention, that the compound of the formula (IV) was obtained and that the carbanion of compound (III) did not rather react with the relatively acidic proton in the α-position to the sulfone functionality of the compound of the formula (II), as might have been expected. Likewise, it was unexpected to find that compound (III) reacted completely with the entire amount of n-butyllithium (or other base) added. If some of this base were still present when the compound of formula (II) was added, they would have been expected to react together to form products other than the desired compound (IV).

The reaction between compounds (IV) and (V) in step (b) of the process of the invention, is also performed in an inert aprotic solvent, preferably tetrahydrofuran, at a temperature in the range of −40° to −10° C. under the influence of a strong base, preferably n-butyllithium. In a preferred embodiment of the invention, the base is used in excess and serves to generate the carbanion from the compound of formula (IV) and, possibly, also to convert the compound of formula (V) above, in situ, to the epoxide of the formula:

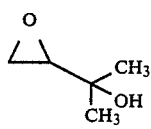

which is believed to be the species reacting with the carbanion of the compound of formula (IV).

In process step (c), the sulfone group may be split off from the complete vitamin D skeleton of the resulting compound of the formula (VI), by any of several methods described in the literature, e.g. by reaction with sodium amalgam, magnesium in methanol, lithium with ethylamine or Raney nickel.

Similarly, in process step (d), the hydroxyprotecting group R in the product of step (c) above, may be removed by any suitable known method, according to the nature of the protecting group. Thus, if R is tert.-butyldimethylsilyl, it may be split off by reacting with tetrabutylammonium fluoride to give the desired 24,25(OH)$_2$D$_3$.

The compounds of formulae (IV) and (VI) are novel and form another aspect of the present invention. In accordance with that aspect there are thus provided compounds of the general formula (X)

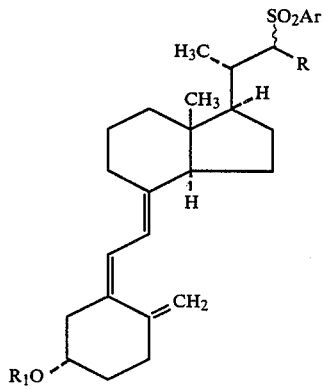

in which Ar and R$_1$ are as defined above, and R is hydrogen or a radical of the formula —CH—CH*(OH)—C(CH$_3$)$_2$OH, having either the (R) or the (S) configuration at the asymmetric carbon atom.

The starting material of formula (II) above can be prepared according to the following reaction scheme:

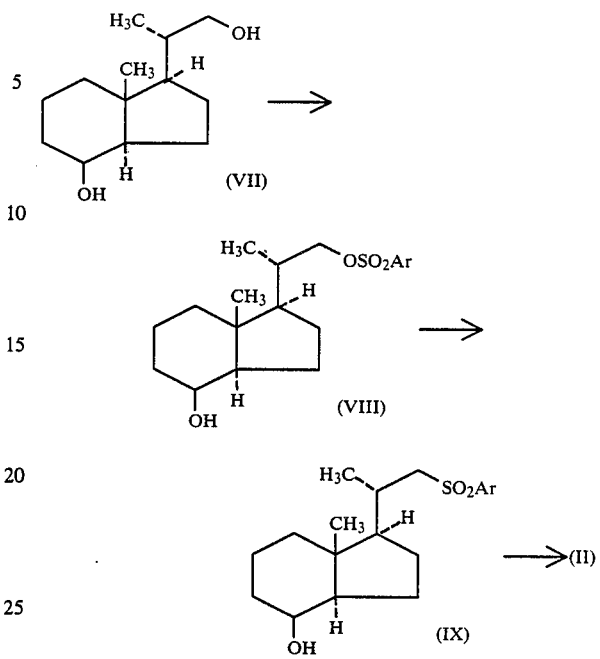

The well known "Inhoffen-Lythgoe diol" (VII) (cf. Inhoffen et al. Ber. 91, 781, (1958)) is selectively arylsulfonated, e.g. with p-toluenesulfonic acid in pyridine, to form (VIII) which is then sulfonated, e.g. using sodium iodide and sodium arylsulfinate in a suitable inert solvent, preferably dimethyl formamide, under known conditions, to form the compound (IX). Compound (IX) is readily oxidized to the ketone (II) using a suitable oxidizing agent such as pyridinium dichromate or pyridinium chlorochromate in an inert solvent such as methylene chloride.

The other starting material of formula (III) is known and can be prepared according to Toh and Okamura, J. Org. Chem., 48, 1414, (1983).

The compounds of formula (V) above can be prepared, e.g. as described in Takayama et al, Tetrahedron Letters, 21, 5027-8, (1980).

The invention will now be further illustrated in more detail in the following non-limiting Examples.

EXAMPLE 1

Preparation of (1R,6R,9R,2'S)-9-(1'-p-toluenesulfonylprop-2'-yl)-1-methyl-bicyclo(4.3.0)nonan-5-ol (IX; Ar=p—CH$_3$—C$_6$H$_4$—).

To a solution of 14.5 g (40 mmole) of (1R,6R,9R,2'S)-9-(1'-p-toluenesulfonyloxyprop-2'-yl)-1-methylbicyclo(4.3.0)nonan-5-ol in 250 ml of dry dimethylformamide under an inert atmosphere were added 60.2 g (400 mmole) of sodium iodide and 10.7 g (60 mmole) of sodium p-toluenesulfinate. The resulting mixture was heated at 80° C. for 2 hours, whereafter 1 liter of ethyl acetate was added. The resulting solution was washed twice with water, once with 5% aqueous sodium thiosulfate and once with brine. The organic layer was dried over anhydrous MgSO$_4$ and concentrated in vacuo. The title compound (7.1 g, 51%) was isolated by recrystallization from ethyl acetate, m.p. 125°-126° C.

Anal. Calcd. for C$_{20}$H$_{30}$O$_3$S: C, 68.53; H, 8.62; S, 9.14; Found: 68.75; 8.65; 9.21.

IR (KBr) 3515, 1295 and 1135 cm$^{-1}$.

NMR (CDCl$_3$): δ4.06 (m, 1H), 2.45 (s, 3H), 1.17 (d, 3H), 0.90 (s, 3H).

EXAMPLE 2

Preparation of (1R,6R,9R,2'S)-9-(1'-p-toluenesulfonylprop-2'-yl)-1-methylbicyclo-(4.3.0)nonan-5-one (II; Ar=p—CH$_3$—C$_6$H$_4$—).

To a stirred suspension of 12.4 g (33 mmole) of pyridinium dichromate in 40 ml of dry methylene chloride was added a solution of 7.6 g (22 mmole) of (1R,6R,9R,2'S)-9-(1'-p-toluenesulfonylprop-2'-yl)-1-methylbicyclo-(4.3.0)nonan-5-ol (from Example 1) in 40 ml of the same solvent. After 2 hours stirring at room temperature, 100 ml of diethyl ether were added and the dark suspension filtered with the aid of suction through a bed of silica gel, washing it through with a 9:1 solution of methylene chloride:diethyl ether. The solvent was removed in vacuo and the title compound (7 g, 92%) was isolated by recrystallization from ethyl acetate, m.p. 148°–149° C.

Anal. Calcd. for C$_{20}$H$_{28}$O$_3$S: C, 68.93; H, 8.10; S, 9.20; Found: 68.61; 8.20; 9.34.

IR(KBr) 1703, 1355, 1190 cm−1.

NMR (CDCl$_3$): δ2.45 (s, 3H); 1.24 (d, 3H), 0.61 (s, 3H).

EXAMPLE 3

Preparation of 3β-tert.-butyldimethylsilyl-22-p-toluenesulfonyl-23,24,25,26,27-pentanorcholecalciferol (IV; R$_1$=TBDMS, Ar=p—CH$_3$—C$_6$H$_4$—).

To a solution of 6.8 g (15.0 mmole) of (S)-(Z)-[2-(5'-tert.-butyldimethylsilyloxy-2'-methylenecyclohexylidene)ethyl]diphenylphosphine oxide in 75 ml of dry tetrahydrofuran at −45° C. were added dropwise 9.3 ml (14.4 mmole) of 1.55M n-butyllithium. After 45 mins. there were added dropwise to the resulting red solution 4.2 g (12.1 mmole) of (1R,6R,9R,2'S)-9-(1'-p-toluenesulfonylprop-2'-yl)-1-methylbicyclo(4.3.0)nonan-5-one (from Example 2) in 60 ml of dry tetrahydrofuran. After an additional 90 mins. at −45° C. the reaction mixture was allowed to warm to room temperature and treated with 30 ml of saturated aqueous sodium bicarbonate and 70 ml of diethyl ether. The mixture was extracted twice with diethyl ether and the combined organic layers washed with brine, dried over anhydrous MgSO$_4$ and the solvent removed in vacuo. The title compound (6.2 g, 88%) was isolated by flash column chromatography, using 12% ethyl acetate in hexane as eluant.

Anal. Calcd. for c$_{35}$H$_{54}$O$_3$SSi: C, 72.11; H, 9.35; S, 5.50; Found: 72.06; 9.06; 5.97.

IR (CHCl$_3$): 1600, 1300, 1135, 1080 cm−1.

NMR (CDCl$_3$): δ6.03 (d of d, 2H); 4.86 (d, 2H); 3.2 (m, 1H), 2.45 (s, 3H); 1.23 (d, 3H); 0.88 (s, 9H); 0.52 (s, 3H).

EXAMPLE 4

Preparation of 3β-tert-butyldimethylsilyl-24(R),25-dihydroxy-22-p-toluenesulfonyl-cholecalciferol (VI; R$_1$=TBDMS; Ar=p—CH$_3$—C$_6$H$_4$—).

To a solution of 4.6 g (16.6 mmole) of 3-methylbutane-1,2(R),3-triol 1-p-toluenesulfonate (V; Ar=-p—CH$_3$—C$_6$H$_4$—) and 4.8 g (8.3 mmole) of 3-tert-butyldimethylsilyl-22-p-toluenesulfonyl-23,24,25,26,27-pentanorcholecalciferol (from Example 3) in 25 ml of dry tetrahydrofuran at −20° C. under an inert atmosphere, were added dropwise 32 ml (49.7 mmole) of 1.55M n-butyllithium. After 1 hour at −20° C., 30 ml of a saturated aqueous ammonium chloride solution were added and the mixture extracted twice with diethyl ether. The combined organic phases were washed successively with saturated aqueous ammonium chloride and brine, dried over anhydrous MgSO$_4$ and concentrated in vacuo to an oil. The title compound (5.2 g, 92%) was isolated by flash column chromatography, using a 1:1 solution of ethyl acetate:hexane as eluant.

Anal. Calcd. for C$_{40}$H$_{64}$O$_5$SSi: C, 70.13; H, 9.42; S, 4.68 Found: 69.88; 9.14; 5.08.

IR (CHCl$_3$): 1600, 1135, 1080 cm−1.

NMR (CDCl$_3$): δ6.02 (d of d, 2H); 4.86 (d, 2H); 2.45 (s, 3H); 1.34 (s, 3H); 1.27 (s, 3H); 0.99 (d, 3H); 0.88 (s, 9H); 0.83 (s, 3H).

EXAMPLE 5

Preparation of 3β-tert-butyldimethylsilyl-24(R),25-dihydroxycholecalciferol.

To a solution of 4.09 g (6 mmole) of 3β-tert.-butyldimethylsilyl-24(R),25-dihydroxy-22-p-toluenesulfonylcholecalciferol (from Example 4) in 80 ml of methanol, were added 17 g (120 mmole) of anhydrous disodium hydrogen phosphate and 55 g (120 mmole) of 5% sodium amalgam and the resulting mixture stirred at 35° C. under an inert atmosphere. After 4 hours the precipitate which formed was removed by filtration and the solvent was removed from the filtrate in vacuo. The residue was extracted with ethyl acetate, the resulting solution was washed with brine, dried over anhydrous MgSO$_4$ and the solvent removed in vacuo. The title compound (2.3 g, 73%) was isolated by flash chromatography eluting with hexane:ethyl acetate (7:3). UV: λmax=265 nm.

EXAMPLE 6

Preparation of 24(R),25-dihydroxycholecalciferol (I).

To a solution of 2.13 g (4 mmole) of 3β-tert-butyldimethylsilyl-24(R),25-dihydroxycholecalciferol (from Example 5) in 40 ml of dry tetrahydrofuran were added 28 ml (28 mmole) of 1M tetrabutylammonium fluoride in tetrahydrofuran, with stirring under an inert atmosphere. After 2 hours at room temperature, the volatiles were removed in vacuo and the residue extracted with ethyl acetate, which was subsequently washed 5 times with water and once with brine, dried over anhydrous MgSO$_4$ and the solvent removed in vacuo. The residue was purified by elution through silica gel with ethyl acetate, with the aid of suction to give the title compound (1.6 g, 95%); m.p. 137°–140° C. (methyl formate). UV: λmax=265 nm.

EXAMPLE 7

Preparation of 24(S),25-dihydroxycholecalciferol (I).

The procedure of Example 4 was followed, except that 3-methylbutane-1,2(S),3-triol 1-p-toluenesulfonate is employed instead of the 2(R) isomer. The 3β-tert-butyldimethylsilyl-24(S),25-dihydroxy-22-p-toluenesulfonyl-cholecalciferol thus obtained, was submitted to the procedures described in Examples 5 and 6, to yield the title compound.

We claim:

1. A process for the stereospecific preparation of a 24(R),25- or 24(S),25-dihydroxycholecalciferol of the general formula (I)

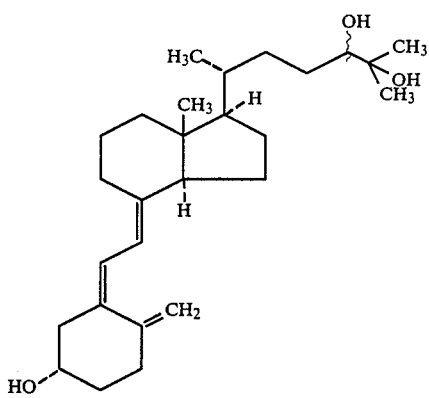

which comprises the steps of:
(a) Condensing a compound of the general formula (II)

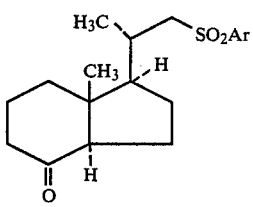

wherein
Ar is monocyclic aryl, having the (1R,6R,9R,2'S) configuration, with the base-generated carbanion derived from a compound of the formula (III)

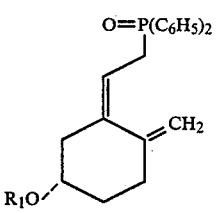

wherein
$R_1$ is a suitable base-stable hydroxy-protecting group, having the (S)-(Z) configuration, to give a compound of the formula (IV)

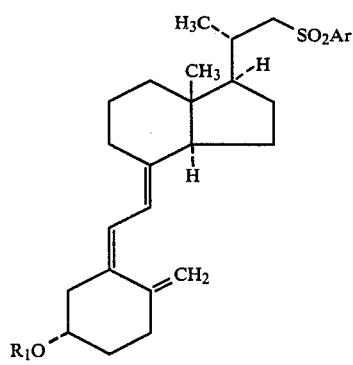

wherein
Ar and $R_1$ are as defined above;
(b) Reacting the base-generated carbanion derived from the compound of formula (IV) above with the 2(R) or 2(S) isomer of 3-methylbutane-1,2,3-triol 1-arylsulfonate of the formula (V)

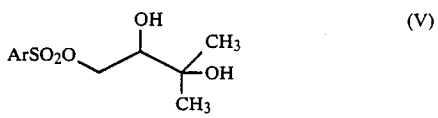

wherein
Ar is as defined above, in the presence of a strong base, to give a compound of the formula (VI)

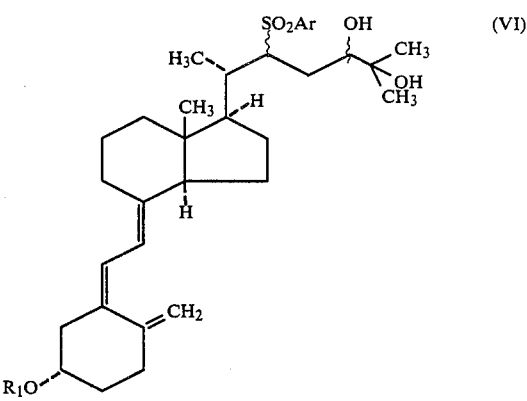

wherein
Ar and $R_1$ are as defined above;
(c) Splitting off the 22-sulfonyl group from the compound of the formula (VI) above by known methods; and
(d) Splitting off the hydroxy-protecting group $R_1$ from the compound thus obtained to yield the desired compound of formula (I) above.

2. A process according to claim 1 wherein the compound of formula (I) prepared is 24(R),25-dihydroxycholecalciferol.

3. A process according to claim 1, wherein $R_1$ in compounds (III), (IV) and (VI) is tert.-butyldimethylsilyl.

4. A process according to claim 1, wherein Ar in compounds (II), (IV) and (VI) is p-tolyl.

5. A process according to claim 1, wherein the condensation reaction in step (a) is conducted in an inert aprotic solvent in the presence of n-butyllithium.

6. A process according to claim 1, wherein the reaction in process step (b) is conducted in an inert aprotic solvent in the presence of excess n-butyllithium.

7. Compounds of the general formula (X)

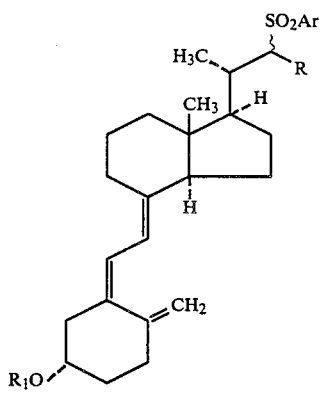

in which Ar is monocyclic aryl, having the (1R,6R,9R,2'S) configuration and $R_1$ is a suitable base-stable hydroxy-protecting group, having the (S)-(Z) configuration and R is hydrogen or a radical of the formula $-CH_2-CH^*(OH)-C(CH_3)_2OH$, having either the (R) or the (S) configuration at the asymmetric carbon atom.

8. Compounds according to claim 7 in which R is the radical $-CH_2-CH^*(OH)-C(CH_3)_2OH$, having either the (R) or the (S) configuration at the asymmetric carbon atom.

9. A compound according to claim 8 having the 24(R) configuration.

10. A process for the preparation of a compound according to claim 8, which comprises reacting the base-generated carbanion derived from the compound of formula (IV)

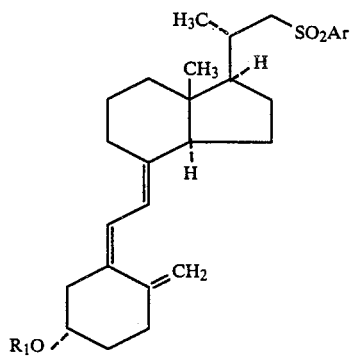

in which Ar and $R_1$ are as defined in claim 1, with the 2(R) or 2(S) isomer of 3-methylbutane-1,2,3-triol 1-arylsulfonate of the formula (V)

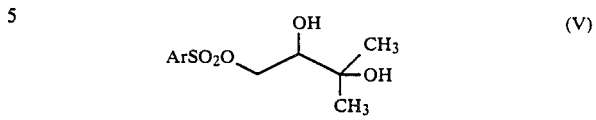

wherein

Ar is as defined above, in the presence of a strong base.

11. A process according to claim 10 wherein the reaction is conducted in an inert aprotic solvent in the presence of excess n-butyllithium.

12. Compounds of the formula (X) in claim 7 in which R is hydrogen.

13. A process for the preparation of a compound according to claim 12, which comprises condensing a compound of the general formula (II)

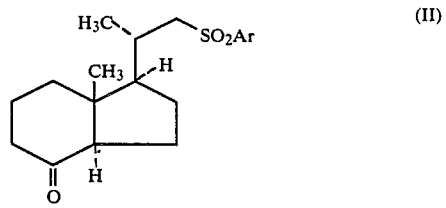

wherein

Ar is monocyclic aryl, having the (1R,6R,9R,2'S) configuration, with the base-generated carbanion derived from a compound of the formula (III)

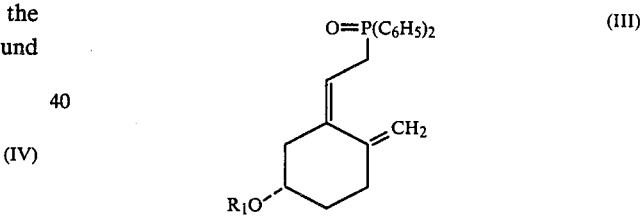

wherein $R_1$ is a suitable base-stable hydroxy-protecting group, having the (S)-(Z) configuration.

14. A process according to claim 13 wherein the condensation is conducted in an inert aprotic solvent in the presence of n-butyllithium.

15. 3β-tert.-Butyldimethylsilyl-22-p-toluenesulfonyl-23,24,25,26,27-pentanorcholecalciferol.

16. 3β-tert.-Butyldimethylsilyl-24(R),25-dihydroxy-22-p-toluenesulfonylcholecalciferol.

* * * * *